(12) United States Patent
Alam

(10) Patent No.: US 9,427,439 B1
(45) Date of Patent: Aug. 30, 2016

(54) METHODS AND COMPOSITIONS FOR RECOVERY FROM STROKE

(71) Applicant: EIP Pharma, LLC, Cambridge, MA (US)

(72) Inventor: John Jahangir Alam, Cambridge, MA (US)

(73) Assignee: EIP Pharma, LLC, Cambridge, MA (US)

( * ) Notice: Subject to any disclaimer, the term of this patent is extended or adjusted under 35 U.S.C. 154(b) by 0 days.

(21) Appl. No.: 14/923,385

(22) Filed: Oct. 26, 2015

(51) Int. Cl.
 *A61K 31/519* (2006.01)
 *A61K 9/00* (2006.01)

(52) U.S. Cl.
 CPC ........... *A61K 31/519* (2013.01); *A61K 9/0053* (2013.01)

(58) Field of Classification Search
 CPC .................................................. A61K 31/519
 USPC ....................................................... 514/248
 See application file for complete search history.

(56) References Cited

U.S. PATENT DOCUMENTS

2012/0245188 A1  9/2012  Huentelman et al.

FOREIGN PATENT DOCUMENTS

WO   WO-2014/145485 A2   9/2014

OTHER PUBLICATIONS

Ferraccioli, Current Opinion in Anti-inflammatory and Immunomodulatory Investigational Drugs (2000), vol. 2(1), pp. 74-77.*
Astolfi, A. et al., p38alpha MAPK and Type I Inhibitors: Binding Site Analysis and Use of Target Ensembles in Virtual Screening, Molecules, 20(9):15842-61 (2015).
Azevedo, R. et al., X-ray structure of p38α bound to TAK-715: comparison with three classic inhibitors, Acta Crystallogr. D Biol. Crystallogr., 68(Pt 8):1041-50 (2012).
Bachstetter, A.D. et al., Attenuation of traumatic brain injury-induced cognitive impairment in mice by targeting increased cytokine levels with a small molecule experimental therapeutic, J. Neuroinflammation, 12:69, 9 pages (2015).
Bachstetter, A.D. et al., the p38α MAPK regulates microglial responsiveness to diffuse traumatic brain injury, J. Neurosci., 33(14):6143-53 (2013).

Barone, F.C. et al., SB 239063, a second-generation p38 mitogen-activated protein kinase inhibitor, reduces brain injury and neurological deficits in cerebral focal ischemia, J. Pharmacol. Exp. Ther., 296(2):312-21 (2001).
Chollet, F., Pharmacologic approaches to cerebral aging and neuroplasticity: insights from the stroke model, Dialogues in Clinical Neuroscience, 15(1):68-76 (2013).
Choudhury, R.G. et al., Involvement of p38 MAPK in reactive astrogliosis induced by ischemic stroke, Brain Res., 1551:45-58 (2014).
Clarkson, A.N. et al., Reducing excessive GABA-mediated tonic inhibition promotes functional recovery after stroke, Nature, 468(7321):305-9 (2010).
Davis, M.I. et al., Comprehensive analysis of kinase inhibitor selectivity, Nat. Biotechnol., 29(11):1046-51, and supplemental figures (2011).
Edwardson, M.A. and Dromerick, A.W., Ischemic stroke prognosis in adults, UpToDate, Official Reprint, Topic 14086, Version 13.0, 14 pages (2015) <www.uptodate.com>.
Goldstein, D.M., et al., Selective p38alpha inhibitors clinically evaluated for the treatment of chronic inflammatory disorders, J. Med. Chem., 53(6):2345-53 (2010).
Grupke, S. et al., Understanding history, and not repeating it. Neuroprotection for acute ischemic stroke: from review to preview, Clin. Neurol. Neurosurg., 129:1-9 (2015).
Hermann, D.M. and Chopp, M., Promoting neurological recovery in the post-acute stroke phase: benefits and challenges, Eur. Neurol., 72(5-6):317-25 (2014).
Paik, N.J. and Yang, E., Role of GABA plasticity in stroke recovery, Neural Regen Res., 9(23):2026-8 (2014).
Piao, C.S. et al., Administration of the p38 MAPK inhibitor SB203580 affords brain protection with a wide therapeutic window against focal ischemic insult, J. Neurosci. Res., 73(4):537-44 (2003).
Verkaar, F. et al., Inhibition of Wnt/β-catenin signaling by p38 MAP kinase inhibitors is explained by cross-reactivity with casein kinase 1δ/ε, Chem. Biol., 18(4):485-94 (2011).
Wang, D.S. et al., Memory deficits induced by inflammation are regulated by alpha5-subunit-containing GABAA receptors, Cell Rep., 2(3):488-96 (2012).
Wu, Z. et al., Tonic inhibition in dentate gyrus impairs long-term potentiation and memory in an Alzheimer's disease model, Nat. Commun., 5:4159, 25 pages (2014).
Arvidsson, A. et al., N-methyl-D-aspartate receptor-mediated increase of neurogenesis in adult rat dentate gyrus following stroke, Eur. J. Neurosci., 14(1):10-8 (2001) [Abstract Only, 1 page].
Author Not Known, Activase (Alteplase), Highlights of Prescribing Information, Genentech, Inc., 16 pages (2015).
Dong, X. et al., Mmp-9, a potential target for cerebral ischemic treatment, Curr. Neuropharmacol., 7(4):269-75 (2009).

* cited by examiner

*Primary Examiner* — Taofiq A Solola
(74) *Attorney, Agent, or Firm* — Choate, Hall & Stewart LLP; Robert N. Sahr

(57) ABSTRACT

The present invention provides methods and compositions for promoting recovery of function from neurologic injury, such as ischemic injury caused by acute stroke.

18 Claims, 9 Drawing Sheets

METHODS AND COMPOSITIONS FOR RECOVERY FROM STROKE

BACKGROUND OF THE INVENTION

Stroke is a prominent cause of serious, long-term disability and the third leading cause of death in the United States. Total health costs for disability due to stroke are estimated at 53.6 billion annually. Ischemic strokes comprise over 88% of all strokes, making them the most common type of cerebrovascular injury. Ischemic conditions in the brain cause neuronal death, leading to sensorimotor and cognitive deficits.

Research and development for the treatment of stroke therapies have until recently focused on approaches that would be utilized within the immediate 24 hours of stroke to either prevent or reduce neuronal cell damage (i.e., as a "neuroprotective agent" for "neuroprotection"). However, several decades of research have only yielded one approved acute stroke therapy by the United States Food and Drug Administration, thrombolysis with tissue plasminogen therapy (tPA). Moreover, the need to administer tPA within the first several hours after stroke, and other limitations, mean that the great majority of patients with an acute stroke do not receive this treatment. Otherwise, numerous pharmaceutical attempts at neuroprotection for stroke have failed in clinical trials (Grupke et al., *Clinical Neurology and Neurosurgery*, 129:1-9 (2015)). As a result, there is an increasing interest in developing therapies that are directed at promoting recovery during the period from the first several days to weeks and several months after stroke; a period during which many patients have some level of recovery, though many remain with residual disability (Hermann & Chopp, *European Neurology*, 72:317-325 (2014)). To date, no pharmaceutical agents have been successfully developed as a treatment to promote neurological recovery after stroke.

SUMMARY OF THE INVENTION

In some embodiments, the present invention comprises methods and compositions comprising a p38-αMAPK inhibitor for promoting recovery of function from a neurologic injury.

In some embodiments, the present invention comprises methods and compositions comprising a p38-αMAPK inhibitor for promoting neurologic recovery from ischemic injury.

In some embodiments, the present invention provides methods and compositions comprising a p38-αMAPK inhibitor to accelerate or promote recovery in a patient who has suffered an acute stroke.

In some embodiments, the present invention provides use of a p38-αMAPK inhibitor in the manufacture of a medicament for promoting recovery of function in a subject that has suffered a neurologic injury. In some embodiments, the present invention provides use of a p38-αMAPK inhibitor in the manufacture of a medicament for promoting neurologic recovery from ischemic injury in a subject.

In some embodiments, the p38-αMAPK inhibitor selectively binds to p38-αMAPK. In some embodiments, a selective p38-αMAPK inhibitor has greater affinity for p38-αMAPK than for p38-βMAPK, p38-γMAPK, and p38-δMAPK. In some embodiments, a selective p38-αMAPK inhibitor has at least 5, 10, 20, 30, or 50 fold greater affinity for p38-αMAPK than for either of p38-βMAPK, p38-γMAPK, or p38-δMAPK. In some embodiments, a selective p38-αMAPK inhibitor has at least 20 fold greater affinity for p38-αMAPK than for either of p38-βMAPK, p38-γMAPK, or p38-δMAPK.

In some embodiments, the p38-αMAPK inhibitor comprises a structure according to Formula I as described herein. In some embodiments, the p38-αMAPK inhibitor comprises a structure according to Formula IIa as described herein. In some embodiments, the p38-αMAPK inhibitor comprises a structure according to Formula IIb as described herein. In some embodiments, the p38-αMAPK inhibitor is VX-745. In some embodiments, the p38-αMAPK inhibitor is SCIO-469. In some embodiments, the p38-αMAPK inhibitor binds to a catalytic site of p38-αMAPK. In some embodiments, the p38-αMAPK inhibitor binds to the adenine ring of adenosine triphosphate (ATP) and competitively inhibits ATP binding. In some embodiments, the p38-αMAPK inhibitor contains a carbonyl group and induces a peptide flip between Met109 and Gly110 amino acid residues of p38-αMAPK. In some embodiments, the p38-αMAPK inhibitor forms hydrogen bonds with the amino acid residue Met109 of p38-αMAPK.

In some embodiments, the neurologic or ischemic injury results from an acute stroke. In some embodiments, the stroke is an ischemic stroke. In some embodiments, the stroke is a thrombotic stroke. In some embodiments, the stroke is an embolic stroke.

In some embodiments, the step of administering is initiated at or greater than 24 hours after the onset of stroke symptoms. In some embodiments, the step of administering is initiated at or greater than 48 hours after the onset of stroke symptoms In some embodiments, the step of administering is initiated at or greater than 72 hours after the onset of stroke symptoms In some embodiments, the step of administering comprises administration of a composition comprising a p38-αMAPK inhibitor. In some embodiments the p38-αMAPK inhibitor is VX-745. In some embodiments, VX-745 is administered at a regular interval. In some embodiments, the regular interval is selected from the group consisting of twice weekly, thrice weekly, every other day, daily, twice daily, and every eight hours.

In some embodiments, the step of administering comprises oral administration.

In some embodiments, the present invention provides pharmaceutical compositions for promoting recovery of function from neurologic injury comprising a therapeutically effective amount of VX-745 and a pharmaceutically acceptable carrier or excipient. In some embodiments, the present invention provides pharmaceutical compositions for promoting neurologic recovery from ischemic injury comprising a therapeutically effective amount of VX-745 and a pharmaceutically acceptable carrier or excipient. In some embodiments, the pharmaceutical compositions are formulated for oral administration.

DEFINITIONS

Figure 1:
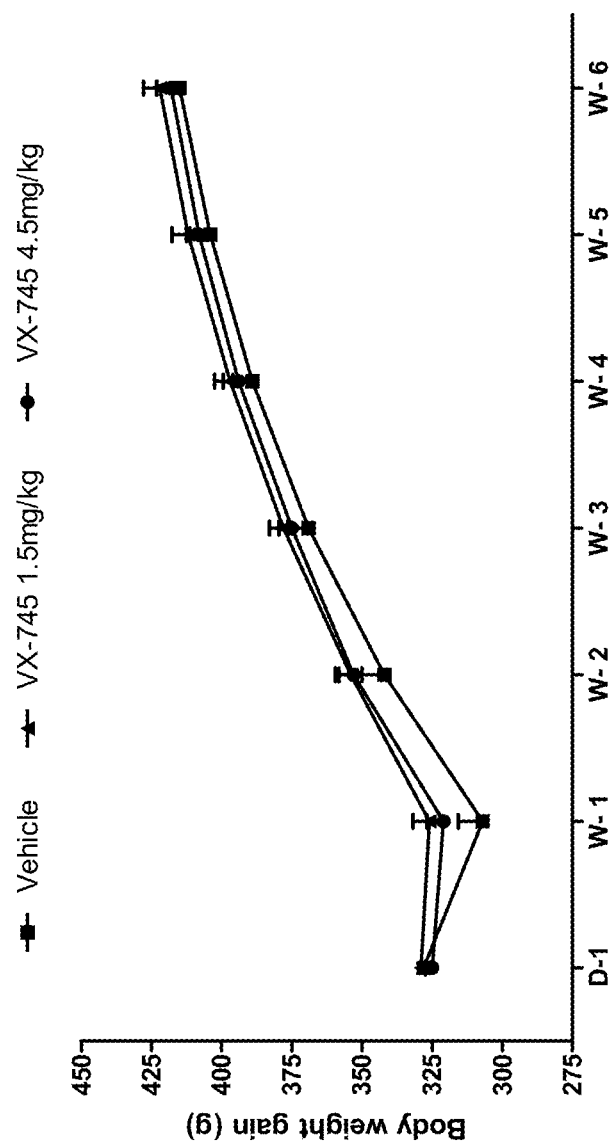
FIG. 1 depicts an exemplary graph showing the distribution of body weight in the study groups throughout a Transient Middle Cerebral Artery Occlusion study.

Carrier.

The term "carrier" refers to any chemical entity that can be incorporated into a composition containing an active agent (e.g., a p38αMAPK inhibitor) without significantly interfering with the stability and/or activity of the agent (e.g., with a biological activity of the agent). In certain embodiments, the term "carrier" refers to a pharmaceutically acceptable carrier. An exemplary carrier herein is water.

Combination.

As used herein, the term "combination," "combined," and related terms refers to a subject's simultaneous exposure to two or more therapeutic agents in accordance with this invention. For example, an agent of the present invention (e.g., a p38-αMAPK inhibitor) may be administered with another therapeutic agent simultaneously or sequentially in separate unit dosage forms or together in a single unit dosage form. Accordingly, the present invention provides, among other things, dosing regimens that involve administering at least an agent of the present invention (e.g., a p38-αMAPK inhibitor), an additional therapeutic agent, and a pharmaceutically acceptable carrier, adjuvant, or vehicle (the pharmaceutically acceptable carrier, adjuvant, or vehicle typically being in association with one or both of the p38α-MAPK inhibitor and the additional therapeutic agent).

Formulation.

The term "formulation" refers to a composition that includes at least one active agent (e.g., p38-αMAPK inhibitor such as VX-745) together with one or more carriers, excipients or other pharmaceutical additives for administration to a patient. In general, particular carriers, excipients and/or other pharmaceutical additives are selected in accordance with knowledge in the art to achieve a desired stability, release, distribution and/or activity of active agent(s) and which are appropriate for the particular route of administration.

Parenteral.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Patient.

The term "patient", as used herein, means a mammal to which a formulation or composition comprising a formulation is administered, and in some embodiments includes humans.

Pharmaceutically Acceptable Carrier, Adjuvant, or Vehicle.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Selective p38-αMAPK Inhibitor.

As used herein, the term "selective p-38-αMAPK inhibitor" refers to a compound that has greater affinity for p38-αMAPK than for p38-βMAPK, p38-γMAPK, and p38-δMAPK. In some embodiments, a selective p38-αMAPK inhibitor has at least 25 fold greater affinity for p38-αMAPK than for p38-βMAPK, p38-γMAPK, and p38-δMAPK.

Therapeutic Agent.

As used herein, the phrase "therapeutic agent" refers to any agent that elicits a desired biological or pharmacological effect when administered to an organism.

Therapeutically Effective Amount and Effective Amount.

As used herein, and unless otherwise specified, the terms "therapeutically effective amount" and "effective amount" of an agent refer to an amount sufficient to provide a therapeutic benefit in the treatment, prevention and/or management of a disease, disorder, or condition, e.g., to delay onset of or minimize (e.g., reduce the incidence and/or magnitude of) one or more symptoms associated with the disease, disorder or condition to be treated. In some embodiments, a composition may be said to contain a "therapeutically effective amount" of an agent if it contains an amount that is effective when administered as a single dose within the context of a therapeutic regimen. In some embodiments, a therapeutically effective amount is an amount that, when administered as part of a dosing regimen, is statistically likely to delay onset of or minimize (reduce the incidence and/or magnitude of) one or more symptoms or side effects of a disease, disorder or condition.

Treat or Treating.

The terms "treat" or "treating," as used herein, refer to partially or completely alleviating, inhibiting, delaying onset of, reducing the incidence of, yielding prophylaxis of, ameliorating and/or relieving a disorder, disease, or condition, or one or more symptoms or manifestations of the disorder, disease or condition.

Unit Dose.

The expression "unit dose" as used herein refers to a physically discrete unit of a formulation appropriate for a subject to be treated (e.g., for a single dose); each unit containing a predetermined quantity of an active agent selected to produce a desired therapeutic effect when administered according to a therapeutic regimen (it being understood that multiple doses may be required to achieve a desired or optimum effect), optionally together with a pharmaceutically acceptable carrier, which may be provided in a predetermined amount. The unit dose may be, for example, a volume of liquid (e.g., an acceptable carrier) containing a predetermined quantity of one or more therapeutic agents, a predetermined amount of one or more therapeutic agents in solid form (e.g., a tablet or capsule), a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. In some embodiments, a unit dose of a p38-αMAPK inhibitor, such as VX-745 is about 1 mg, 3 mg, 5 mg, 10 mg, 15 mg, 20 mg, 25 mg, 30 mg, 35 mg, 40 mg, 45 mg, 50 mg, 100 mg or 125 mg.

Detailed Description of Certain Embodiments

Immediate treatment for patients suffering from stroke is often impossible in the clinical setting and physicians urgently need new treatment strategies.

The present invention provides, among other things, compositions and methods for treating neurologic injury in a subject. In particular, the present invention provides methods for promoting recovery of function in a subject that has suffered a neurologic injury, such as from an acute ischemic stroke, by administering a composition comprising a selective p38-αMAPK inhibitor. In some embodiments, the invention provides methods for promoting neurologic recovery from ischemic injury by administering a composition comprising a selective p38-αMAPK inhibitor.

Various aspects of the invention are described in detail in the following sections. The use of sections is not meant to limit the invention. Each section can apply to any aspect of the invention. In this application, the use of "or" means "and/or" unless stated otherwise.

p38-αMAPK Inhibitors

In some embodiments, the p38-αMAPK inhibitor selectively binds to p38-αMAPK. A selective p38-αMAPK inhibitor has greater affinity for p38-αMAPK than for p38-βMAPK, p38-γMAPK, and p38-δMAPK. In some embodiments, a selective p38-αMAPK inhibitor has at least 5, 10, 20, 30, or 50 fold greater affinity for p38-αMAPK than for either of p38-βMAPK, p38-γMAPK, or p38-δMAPK.

In some embodiments the p38-αMAPK inhibitor binds to a catalytic site of p38-αMAPK. In some embodiments, the p38-αMAPK inhibitor binds to the adenine ring of adenosine triphosphate (ATP) and competitively inhibits ATP binding. In some embodiments, the p38-αMAPK inhibitor contains a carbonyl group and induces a peptide flip between Met109 and Gly110 amino acid residues of p38-αMAPK. In some embodiments, the p38-αMAPK inhibitor forms hydrogen bonds with the amino acid residue Met109 of p38-αMAPK. In some embodiments the p38-αMAPK inhibitor has one or more, or all of the above properties.

Compounds of this invention, and pharmaceutically acceptable compositions thereof, are effective as inhibitors of p38-αMAPK. In some embodiments, such compounds include those of formula I:

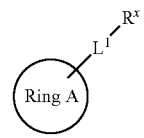

I or a pharmaceutically acceptable salt thereof, wherein:

Ring A is an optionally substituted ring selected from phenyl; a 5-6 membered monocyclic heteroaryl ring have 1-4 heteroatoms independently selected from nitrogen, oxygen, and sulfur; a 6-10 membered saturated or partially unsaturated bicyclic heterocyclic ring having 1-5 heteroatoms independently selected from nitrogen, oxygen, and sulfur; and a 7-10 membered bicyclic heteroaryl ring having 1-5 heteroatoms independently selected from nitrogen, oxygen, and sulfur;

$L^1$ is a covalent bond or an optionally substituted straight or branched bivalent $C_{1-6}$ hydrocarbon chain, wherein one or more methylene units may be optionally replaced by —NR—, —O—, —S—, —C(O)—, or an optionally substituted bivalent ring selected from phenylene; a 3-8 membered saturated or partially unsaturated monocyclic heterocyclic ring having 1-4 heteroatoms independently selected from nitrogen, oxygen, and sulfur; a 5-6 membered monocyclic heteroaryl ring having 1-4 heteroatoms independently selected from nitrogen, oxygen, and sulfur, a 6-10 membered saturated or partially unsaturated bicyclic heterocyclic ring having 1-5 heteroatoms independently selected from nitrogen, oxygen, and sulfur; and a 7-10 membered bicyclic heteroaryl ring having 1-5 heteroatoms independently selected from nitrogen, oxygen, and sulfur;

each R is independently hydrogen or an optionally substituted group selected from $C_{1-6}$ aliphatic; a 3-8 membered saturated or partially unsaturated monocyclic carbocyclic ring; phenyl; an 8-10 membered bicyclic aryl ring; a 3-8 membered saturated or partially unsaturated monocyclic heterocyclic ring having 1-4 heteroatoms independently selected from nitrogen, oxygen, and sulfur; a 5-6 membered monocyclic heteroaryl ring having 1-4 heteroatoms independently selected from nitrogen, oxygen, and sulfur; a 6-10 membered saturated or partially unsaturated bicyclic heterocyclic ring having 1-5 heteroatoms independently selected from nitrogen, oxygen, and sulfur; and a 7-10 membered bicyclic heteroaryl ring having 1-5 heteroatoms independently selected from nitrogen, oxygen, and sulfur, and $R^x$ is independently R, halogen, —$NR_2$, OR, or an optionally substituted ring selected from phenyl; a 5-6 membered monocyclic heteroaryl ring have 1-4 heteroatoms independently selected from nitrogen, oxygen, and sulfur; a 6-10 membered saturated or partially unsaturated bicyclic heterocyclic ring having 1-5 heteroatoms independently selected from nitrogen, oxygen, and sulfur; and a 7.10 membered bicyclic heteroaryl ring having 1-5 heteroatoms independently selected from nitrogen, oxygen, and sulfur.

In some embodiments, Ring A is phenyl. In some embodiments, Ring A is optionally substituted phenyl. In some embodiments Ring A is pyridinyl. In some embodiments, Ring A is optionally substituted pyridinyl.

In some embodiments, Ring A is pyrimidopyridazinyl. In some embodiments, Ring A is optionally substituted pyrimidopyridazinyl. In some embodiments, Ring A is 6H-pyrimido[1,6-b]pyridazinyl. In some embodiments, Ring A is optionally substituted 6H-pyrimido[1,6-b]pyridazinyl.

In some embodiments, Ring A is pyrimidopyridazinone. In some embodiments, Ring A is optionally substituted pyrimidopyridazinone. In some embodiments, Ring A is pyrimidopyridazin-6-one. In some embodiments, Ring A is optionally substituted pyrimidopyridazin-6-one. In some embodiments, Ring A is 6H-pyrimido[1,6-b]pyridazin-6-one. In some embodiments, Ring A is optionally substituted 6H-pyrimido[1,6-b]pyridazin-6-one.

In some embodiments, $L^1$ is a covalent bond. In some embodiments $L^1$ is an optionally substituted straight or branched bivalent $C_{1-6}$ hydrocarbon chain, wherein one or more methylene units may be optionally replaced by —NR—, —O—, —S—, —C(O)—, or an optionally substituted bivalent ring selected from phenylene; a 3-8 membered saturated or partially unsaturated monocyclic heterocyclic ring having 1-4 heteroatoms independently selected from nitrogen, oxygen, and sulfur; a 5-6 membered monocyclic heteroaryl ring having 1-4 heteroatoms independently selected from nitrogen, oxygen, and sulfur; a 6-10 membered saturated or partially unsaturated bicyclic heterocyclic ring having 1-5 heteroatoms independently selected from nitrogen, oxygen, and sulfur; and a 7-10 membered bicyclic heteroaryl ring having 1-5 heteroatoms independently selected from nitrogen, oxygen, and sulfur.

In some embodiments, $L^1$ is an optionally substituted straight or branched bivalent $C_{1-6}$ hydrocarbon chain, wherein one or more methylene units may be optionally replaced by —NR—, —O—, —S—, —C(O)—. In some embodiments, $L^1$ is an optionally substituted straight or branched bivalent $C_{1-3}$ hydrocarbon chain, wherein one or more methylene units may be optionally replaced by —NR—, —O—, —S—, —C(O)—. In some embodiments, $L^1$ is an optionally substituted straight or branched bivalent $C_1$ hydrocarbon chain, wherein one methylene unit is replaced by —NR—. In some embodiments, $L^1$ is an optionally substituted straight or branched bivalent $C_1$ hydrocarbon chain, wherein one methylene unit is replaced by —S—. In some embodiments, $L^1$ is an optionally substituted straight or branched bivalent $C_1$ hydrocarbon chain, wherein one methylene unit is replaced by —C(O)—.

In some embodiments, $L^1$ is selected from the following structures:

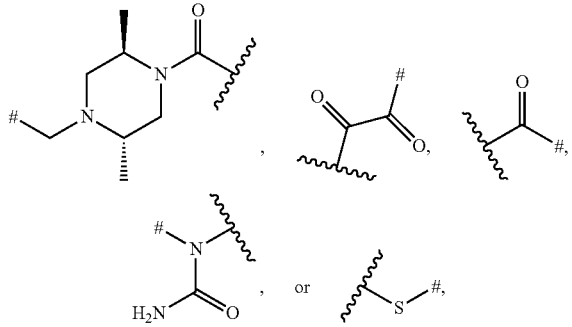

wherein

represents the point of attachment to Ring A and # represents the point of attachment to $R^x$.

In some embodiments, $R^x$ is R. In some embodiments, $R^x$ is hydrogen. In some embodiments, $R^x$ is $C_{1-6}$ aliphatic. In some embodiments, $R^x$ is methyl. In some embodiments, $R^x$ is optionally substituted $C_{1-6}$ aliphatic. In some embodiments, $R^x$ is optionally substituted methyl. In some embodiments, $R^x$ is halogen. In some embodiments, $R^x$ is fluorine. In some embodiments, $R^x$ is chlorine. In some embodiments, $R^x$—$NR_2$. In some embodiments, $R^x$ is —$NH_2$. In some embodiments, $R^x$ is —$NMe_2$. In some embodiments, $R^x$ is phenyl. In some embodiments, $R^x$ is optionally substituted phenyl. In some embodiments, $R^x$ is phenyl, substituted with 1 halogen. In some embodiments, $R^x$ is phenyl, substituted with 1 fluorine atom. In some embodiments, $R^x$ is phenyl, substituted with 1 chlorine atom. In some embodiments, $R^x$ is phenyl, substituted with 2 halogens. In some embodiments, $R^x$ is phenyl, substituted with 2 fluorine atoms. In some embodiments, $R^x$ is phenyl, substituted with 2 chlorine atoms. In some embodiments, $R^x$ is selected from the following structures:

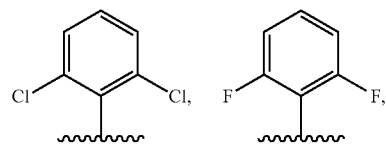

-continued

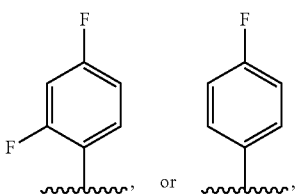

wherein

represents the point of attachment to $L^1$.

Exemplary compounds of formula I are set forth below:

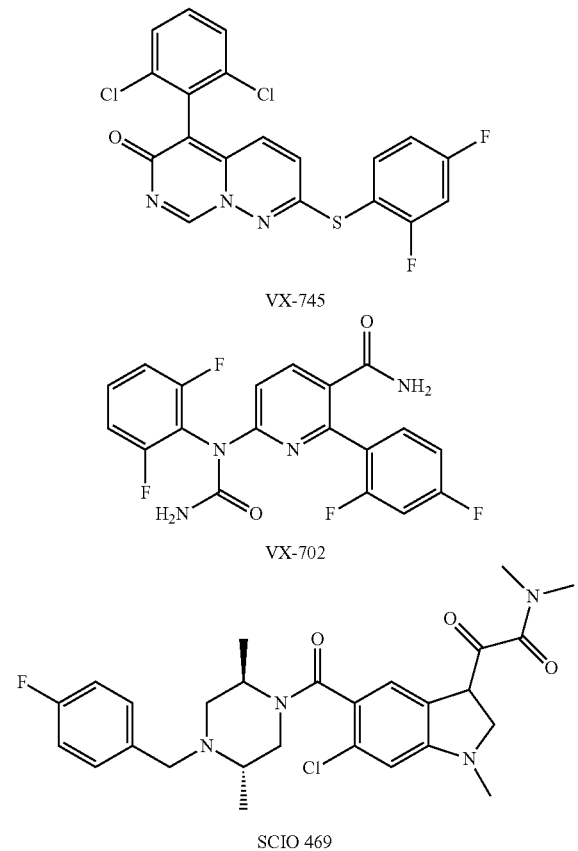

VX-745

VX-702

SCIO 469

In some embodiments, compounds of the present invention include those disclosed within U.S. Pat. No. 8,338,412, the entirety of which is incorporated herein by reference. In some embodiments, compounds of the present invention include those of formula IIa or IIb:

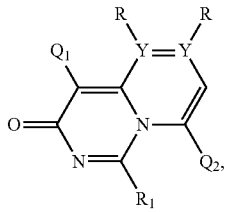

IIa

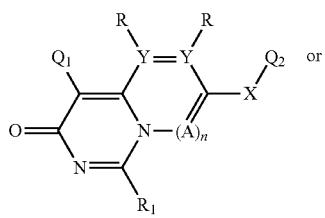

IIb wherein each of $Q_1$ and $Q_2$ are independently selected from 5-6 membered aromatic carbocyclic or heterocyclic ring systems, or 8-10 membered bicyclic ring systems comprising aromatic carbocyclic rings, aromatic heterocyclic rings or a combination of an aromatic carbocyclic ring and an aromatic heterocyclic ring.

The rings that make up Qt are substituted with 1 to 4 substituents, each of which is independently selected from halo; $C_1$-$C_3$ alkyl optionally substituted with $NR'_2$, $OR'$, $CO_2R'$ or $CONR'_2$; O—($C_1$-$C_3$)-alkyl optionally substituted with $NR'_2$, $OR'$, $CO_2R'$ or $CONR'_2$; $NR'_2$; $OCF_3$; $CF_3$; $NO_2$; $CO_2R'$; $CONHR'$; $SR'$; $S(O_2)N(R')_2$; $SCF_3$; $CN$; $N(R')C(O)R^4$; $N(R')C(O)OR^4$; $N(R')C(O)C(O)R^4$; $N(R')S(O_2)R^4$; $N(R')R^4$; $N(R^4)_2$; $OR^4$; $OC(O)R^4$; $OP(O)_3H_2$; or $N$=$CH$—$N(R')_2$. The rings that make up $Q_2$ are optionally substituted with up to 4 substituents, each of which is independently selected from halo; $C_1$-$C_3$ straight or branched alkyl optionally substituted With $NR'_2$, $OR'$, $CO_2R'$, $S(O_2)N(R')_2$, $N$=$CH$—$N(R')_2$, $R^3$, or $CONR'_2$; O—($C_1$-$C_3$)-alkyl; O—($C_1$-$C_3$)-alkyl optionally substituted with $NR'_2$, $OR'$, $CO_2R'$, $S(O_2)N(R')_2$, $N$=$CH$—$N(R')_2$, $R^3$, or $CONR'_2$; $NR'_2$; $OCF_3$; $CF_3$; $NO_2$; $CO_2R'$; $CONHR'$; $R^3$; $OR^3$; $NHR^3$; $SR^3$; $C(O)R^3$; $C(O)N(R')R^3$; $C(O)OR^3$; $SR'$; $S(O_2)N(R')_2$; $SCF_3$; $N$=$CH$—$N(R')_2$; or $CN$.

$R'$ is selected from hydrogen, ($C_1$-$C_3$)-alkyl; ($C_2$-$C_3$)-alkenyl or alkynyl; phenyl or phenyl substituted with 1 to 3 substituents independently selected from halo, methoxy, cyano, nitro, amino, hydroxy, methyl or ethyl.

$R^3$ is selected from 5-6 membered aromatic carbocyclic or heterocyclic ring systems.

$R^4$ is ($C_1$-$C_4$)-alkyl optionally substituted With $N(R')_2$, $OR'$, $CO_2R'$, $CON(R')_2$, or $SO_2N(R^2)_2$; or a 5-6 membered carbocyclic or heterocyclic ring system optionally substituted with $N(R')_2$, $OR'$, $CO_2R'$, $CON(R')_2$, or $SO_2N(R^2)_2$.

X is selected from —S—, —O—, —S($O_2$)—, —S(O)—, —S($O_2$)—N($R^2$)—, —N($R^2$)—S($O_2$)—, —N($R^2$)—C(O)O—, —O—C(O)—N($R^2$), —C(O)—, —C(O)O—, —O—C(O)—, —C(O)—N($R^2$)—, —N($R^2$)—C(O)—, —N($R^2$)—C($R^2$)$_2$—, or —C(O$R^2$)$_2$—.

Each R is independently selected from hydrogen, —$R^2$, —N($R^2$)$_2$, —O$R^2$, S$R^2$, —C(O)—N($R^2$)$_2$, —S($O_2$), —N($R^2$)$_2$, or —C(O)—O$R^2$, wherein two adjacent R are optionally bound to one another and, together with each Y to which they are respectively bound, form a 4-8 membered carbocyclic or heterocyclic ring;

When the two R components form a ring together with the Y components to which they are respectively bound, it will obvious to those skilled in the art that a terminal hydrogen from each unfused R component will be lost. For example, if a ring structure is formed by binding those two R components together, one being —NH—$CH_3$ and the other being —$CH_2$—$CH_3$, one terminal hydrogen on each R component (indicated in bold) will be lost. Therefore, the resulting portion of the ring structure will have the formula —NH—$CH_2$—$CH_2$—$CH_2$—.

$R^2$ is selected from hydrogen, ($C_1$-$C_3$)-alkyl, or ($C_2$-$C_3$) alkenyl; each optionally substituted with —N(R')$_2$, —OR', SR', —C(O)—N(R')$_2$, —S($O_2$)—N(R')$_2$, —C(O)—OR', or $R^3$.

Y is N or C;

A, if present, is N or CR';

n is 0 or 1;

$R^1$ is selected from hydrogen, ($C_1$-$C_3$)-alkyl, OH, or O—($C_1$-$C_3$)-alkyl. It will be apparent to those of skill in the art that if $R^1$ is OH, the resulting inhibitor may tautomerize resulting in compounds of the formula:

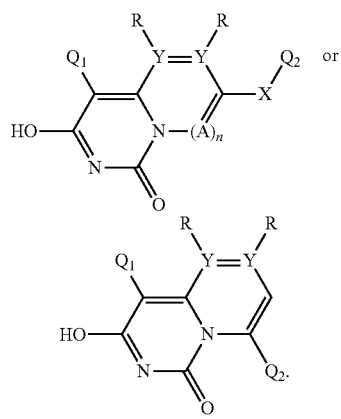

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR' (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —($CH_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein, the term "lactam" refers to cyclic amides of amino carboxylic acids, having a 1-azacycloalkan-2-one structure, or analogues having unsaturation or heteroatoms replacing one or more carbon atoms of the ring. An "α-lactam," refers to a lactam comprised of a 3-membered ring. A "β-lactam," refers to a lactam comprised of a 4-membered ring. A "γ-lactam," refers to a lactam comprised of a 5-membered ring. A "δ-lactam," refers to a lactam comprised of a 6-membered ring. An "ε-lactam," refers to a lactam comprised of a 7-membered ring.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —O$(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$—; —$(CH_2)_{0-4}SC(O)R°$; —$(CH_2)_{0-4}C(O)NR°_2$; —$C(S)NR°_2$; —$C(S)SR°$; —SC(S)SR°, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—N(R°)_2$; or —$(C_{1-4}$ straight or branched alkylene)C(O)O—N(R°)_2$, wherein each $R°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$, —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR^•$, or —$SSR^•$; wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Science*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

VX-745

VX-745 is a selective small-molecule inhibitor of p38-αMAPK previously developed by Vertex Pharmaceuticals for the treatment of rheumatoid arthritis (RA).

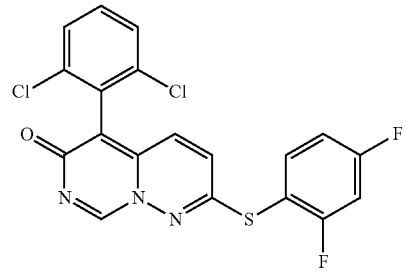

VX-745

The inhibition of MAPK by VX-745 blocks the downstream synthesis of inflammatory cytokines TNF-α and IL-1β. The whole blood IC50 for VX-745 is 150 to 180 nM, or between 65 and 80 ng/mL (Duffy et al., *ACS Medicinal Chemistry Letters*, 2(10);758-763 (2011)), while the IC50 for inhibition of cytokine signaling is half that for cytokine production (Alam, *Journal of Alzheimer's Disease*, 28:219-227 (2015)). VX-745 preferentially distributes to the brain with drug concentrations in the brain in pre-clinical studies being approximately two-fold higher than in the blood.

Stroke

In some embodiments, provided compositions are used in the treatment of stroke. A stroke occurs when the blood supply to part of the brain is interrupted or severely reduced, depriving brain tissue of oxygen and nutrients. Within minutes, brain cells begin to die.

It is important to note when signs and symptoms of a stroke begin because the length of time they have been present may guide treatment decisions. Signs and symptoms of stroke include trouble with walking, trouble with speaking and understanding, paralysis or numbness of the face, arm or leg, trouble with seeing in one or both eyes, and headache. A stroke can sometimes cause temporary or permanent disabilities, depending on how long the brain suffers a lack of blood flow and which part was affected. Complications may include paralysis or loss of muscle movement, difficulty talking or swallowing, memory loss or thinking difficulties, emotional problems, visual field deficits, sensory and motor deficits, pain, and changes in behavior and self-care.

A stroke occurs when the blood supply to the brain is interrupted or reduced. This deprives the brain of oxygen and nutrients, which can cause brain cells to die. A stroke may be caused by a blocked artery (ischemic stroke) or a leaking or burst blood vessel (hemorrhagic stroke). Some people may experience a temporary disruption of blood flow through their brain (transient ischemic attack). The majority of strokes are ischemic strokes. Ischemic strokes occur when the arteries to the brain become narrowed or blocked, causing severely reduced blood flow (ischemia). The most common ischemic strokes include: thrombotic stroke (blood clot in one the arteries that supply blood to the brain) and embolic stroke (blood clot or other debris forms away from the brain—commonly in the heart—and travels through the bloodstream to lodge in a narrow brain artery).

Hemorrhagic stroke occurs when a blood vessel in the brain leaks or ruptures. Brain hemorrhages can result from many conditions that affect the blood vessels, including uncontrolled high blood pressure (hypertension) and weak spots in blood vessel walls (aneurysms). A less common cause of hemorrhage is the rupture of an arteriovenous malformation (AVM)—an abnormal tangle of thin-walled blood vessels, present at birth. The types of hemorrhagic stroke include: intracerebral hemorrhage (blood vessel in brain bursts and spills into surrounding brain tissue, damaging brain cells) and subarachnoid hemorrhage (artery on or near the surface of the brain bursts and spills into the space between the brain and the skull).

A transient ischemic attack (TIA)—also called a ministroke—is a brief episode of symptoms similar to those one would have in a stroke. A transient ischemic attack is caused by a temporary decrease in blood supply to part of the brain. TIAs often last less than five minutes. Like an ischemic stroke, a TIA occurs when a clot or debris blocks blood flow to part of the brain. A TIA typically doesn't leave lasting symptoms because the blockage is temporary.

Only a minority of survivors of a moderate to severe stroke recover fully and many stroke survivors have some level of residual motor or cognitive deficit. Stroke is the leading cause of long-term disability in the United States and Europe.

Recovery from Stroke

The prognosis for recovery from stroke is influenced by several factors such as stroke severity, type of stroke, location of infarct, comorbidity with other disorders or other clinical complications. The majority of survivors of an acute stroke demonstrate some level of neurological recovery during the three to six months after the initial event. The estimated 30-day case fatality rate ranges from 16-23 percent for patients after a first ischemic stroke. At six months after stroke, persistent neurological deficits observed include hemiparesis and cognitive deficits in 40-50 percent of patients. Hemianopsia, aphasia, or sensory deficits are observed in 15-20 percent of patients. Disability outcomes include depression, inability to walk without assistance, and social impairments in approximately 30 percent of patients, and institutional care in approximately 25 percent of patients. (Edwardson et al., UpToDate website, available on the world wide web at uptodate.com; updated at Jun. 10, 2015.)

Neurologic recovery refers to recovery of neurological impairment attributable to brain recovery, including but not limited to neuronal growth, axonal sprouting, synaptogenesis, increased synaptic strength, regeneration, plasticity and/or reorganization of neuronal networks. Neurologic impairment may be measured qualitatively and/or quantitatively by methods known to clinicians. For example, neurologic function after stroke may be quantitated by use of the National Institutes of Health Stroke Scale (NIHSS), which measures neurologic impairment using a 15-item scale that includes assessment of level of consciousness (i.e., alertness), level of consciousness questions (e.g., current month and age of patient), level of consciousness commands (e.g., eye opening and grip), gaze (palsy or paresis), vision, facial palsy, motor ability of arms, motor ability of legs, limb ataxia, sensory loss, language function (i.e., aphasia), dysarthria, and extinction and inattention (i.e., visual, tactile, spatial, or personal neglect). In some embodiments, neurologic recovery from injury or stroke is measured in a subject by assessment of one or more scores by a subject on a neurologic exam as compared to the subject's prior baseline score. In some embodiments, neurologic recovery from stroke is measured by comparison of a subject's score to a reference score from a cohort of subjects similarly afflicted.

In some embodiments, neurological recovery is assessed by neuroimaging, for example, magnetic resonance imaging (MRI), functional magnetic resonance imaging (fMRI), computerized tomography (CT) scans, positron emission tomography (PET) scans, and the like.

Functional recovery from stroke refers to recovery of activities, for example, improvement in mobility and activities of daily living. Functional recovery from stroke may be measured by an improvement in a stroke index score known to clinicians, for example, the Barthel Index of Activities of Daily Living or Rankin Scale, modified Rankin Scale, and the like. The Barthel Index of Activities of Daily Living measures basic aspects of self-care and physical dependency, such as bowel control, bladder control, grooming, toilet use, feeding, mobility, dressing, stair climbing, and bathing. The modified Rankin Scale measures functional independence on a seven grade scale.

In some embodiments, recovery of function from stroke is assessed qualitatively, such as by mortality, ability to return to work or school, live independently, or participate in social and recreational activities.

P38MAPK Inhibition to Promote Recovery

Brain-derived neurotrophic factor (BDNF) appears to have a role in promoting recovery after stroke by promoting neuronal plasticity (Plougman et al., *Stroke,* 40(4):1490-1495 (2009); Berretta et al., *Expert Review of Neurotherapeutics,* 14(11): 1-10 (2014)). The inflammatory cytokine interleukin-1 beta (IL-1β) is upregulated during and after ischemic stroke and has been shown to inhibit the effects of BDNF on neuronal/synaptic plasticity (Tong et al., *Journal of Neuroscience,* 32(49): 17714-17724 (2012)), as well the effect of BDNF on increasing energy utilization and efficiency (Markham et al., *European Journal of Neuroscience,* 35(3):366-374 (2012)). Moreover, the effects of IL-1β on BDNF-dependent synaptic plasticity appear to be dependent on the intracellular signaling protein kinase, p38 mitogen-activated protein kinase (p38 MAPK). Accordingly, inhibition of p38 MAPK activity may promote neuronal/synaptic plasticity in the post-stroke setting through reversing the IL-1β-mediated inhibition of the beneficial effects of BDNF. Antagonists of p38 MAPK have previously demonstrated therapeutic activity in animal models of stroke, but only if administered as a neuroprotective agent within 12 hours of ischemia. Indeed, when administered 24-hours after stroke one particular p38 MAPK inhibitor, SB203850, showed no significant effect on recovery from neurologic deficit (Piao et al., *Journal of Neuroscience Research,* 73:537-544 (2003)). Nevertheless, as VX-745 is a selective antagonist of p38-αMAPK that inhibits IL-1β production and signaling in vitro, and the need for drug candidates that would promote neurological recovery after stroke, VX-745 was evaluated for its potential to promote neurologic recovery after ischemic stroke in animal.

Methods of the Invention

In certain embodiments, a provided method comprises administering to a patient in need thereof VX-745, or a pharmaceutically acceptable composition thereof, at a dose providing a blood concentration of between about 15 and about 45 ng/mL. In some embodiments, a provided method comprises administering to a patient in need thereof a dose of VX-745, or a pharmaceutically acceptable composition thereof, providing a blood concentration of between about 20 and about 40 ng/mL, or between about 25 and about 35 ng/mL, or between about 30 and about 40 ng/mL.

In certain embodiments, the present invention provides methods for promoting recovery of function from a neurologic injury and/or promoting neurologic recovery from ischemic injury comprising administering to a patient in need thereof a dose of VX-745, or a pharmaceutically acceptable composition thereof providing a blood concentration of between about 15 and 45 ng/mL, or between about 20 and about 40 ng/mL, or between about 25 and about 35 ng/mL, or between about 30 and about 40 ng/mL.

In certain embodiments, the present invention provides methods for promoting recovery of function or treating ischemic injury in a subject with a composition comprising VX-745 after the subject has suffered a stroke. In some embodiments, treatment is initiated more than 6, 12, 16, 20, 24, 28, 32, 36, 40, 48, 60, or 72 hours after the stroke. In some embodiments, treatment is initiated approximately 24 hours after a stroke. In some embodiments, treatment is initiated approximately 48 hours after a stroke. In some embodiments, treatment is initiated approximately 72 hours after a stroke.

Pharmaceutical Compositions

In some embodiments, a provided method comprises administering to a patient a pharmaceutical composition comprising VX-745 together with one or more therapeutic agents and a pharmaceutically acceptable carrier, adjuvant, or vehicle. In some embodiments, the present invention provides a pharmaceutical composition comprising a dose of VX-745 together with one or more therapeutic agents and a pharmaceutically acceptable carrier, adjuvant, or vehicle, wherein the dose of VX-745 results in a blood concentration of between about 5 and 45 ng/mL, between about 10 and 45 ng/mL, between about 15 and 45 ng/mL, or between about 20 and about 40 ng/mL, or between about 25 and about 35 ng-mL, or between about 30 and about 40 ng/mL. In some embodiments, the dose of VX-745 results in a blood concentration of between about 5 and 35 ng/mL, between about 10 and 30 ng/mL, between about 10 and 25 ng/mL, between about 5 and 20 ng/mL, or between about 10 and 20 ng/mL.

In certain embodiments, pharmaceutically acceptable compositions of this invention are formulated for oral administration. Pharmaceutically acceptable compositions of this invention may be orally administered in any orally acceptable dosage form including, but not limited to, capsules, caplets, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

The quantities of the compounds of the present invention that are combined with the carrier materials to produce a composition in a single dosage form will vary depending upon the patient and the particular mode of administration. Preferably, provided compositions should be formulated so that a dosage of between 1-50 mg/day of VX-745 can be administered to a patient receiving these compositions. Examples of compositions include compositions formulated to administer dosages of between 1-10 mg, 10-25 mg or 25-50 mg per day of VX-745 to the patient receiving these compositions. In other embodiments of the invention, compositions include compositions formulated to administer dosages of between 3-5 mg, 5-10 mg, 10-20 mg, 20-30 mg, 30-40 mg or 40-50 mg, per day of the inhibitor to the patient receiving these compositions. In some embodiments, the composition is formulated into doses containing 1 mg, 3 mg, 5 mg, 10 mg, 20 mg, 25 mg, 30 mg, 40 mg, 50 mg, or 125 mg of the active composition. Dosing regimens for these formulations may include but are not limited to single administration dosing, once, twice, or three times daily dosing, weekly dosing, and monthly dosing. In some embodiments, a provided composition is formulated to provide 40 mg/day of VX-745. In some embodiments, a provided composition is formulated to provide 125 mg/day of VX-745.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Dosing

In some embodiments, a compositions are administered in a therapeutically effective amount and/or according to a dosing regimen that is correlated with a particular desired outcome (e.g., with treating or reducing risk for disease).

Any provided composition as described herein may be administered by any appropriate route. In some embodiments, provided compositions as described herein is administered intravenously. In some embodiments, provided compositions as described herein is administered subcutaneously. As used herein, the term "subcutaneous tissue" is defined as a layer of loose, irregular connective tissue immediately beneath the skin. For example, the subcutaneous administration may be performed by injecting a composition into areas including, but not limited to, thigh region, abdominal region, gluteal region, or scapular region. In other embodiments, provided compositions as described herein is administered by direct administration to a target tissue, such as heart or muscle (e.g., intramuscular), nervous system (e.g., direct injection into the brain; intraventricularly; intrathecally), or other target tissue such as the liver, kidney, etc. Alternatively, provided compositions as described herein can be administered via inhalation, intraperitoneally, parenterally, intradermally, transdermally, or transmucosally (e.g., orally or nasally). More than one route can be used concurrently, if desired.

In some embodiments, provided compositions are administered in a therapeutically effective amount and/or according to a dosing regimen that is correlated with a particular desired outcome (e.g., recovery from ischemic injury).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of ischemic injury, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce one or more symptoms by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100%. Alternatively or additionally, in some embodiments, an appropriate dose or amount is determined through use of one or more in vitro or in vivo assays to help identify desirable or optimal dosage ranges or amounts to be administered.

In various embodiments, provided compositions are administered at a therapeutically effective amount. As used herein, the term "therapeutically effective amount" or "therapeutically effective dosage amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, provided compositions are administered at a dose that delivers to the blood stream sufficient amount of VX-745 to inhibit p38 MAPK-mediated intracellular signaling events after activation of cytokines and other receptors. In some embodiments, provided compositions are administered at a dose that achieves blood concentrations one-half, one-third, one-fourth, one-fifth, one-sixth, one-seventh, or one-eighth the blood concentration required to reduce inflammation and treat a disorder other than a neurological disorder resulting from ischemic injury in accordance with the present invention. For example, the mean blood concentration of VX-745 in the treatment of rheumatoid arthritis is approximately 75 ng/mL, consistent with whole blood $IC_{50}$ for VX-745 inhibition of cytokine production (anti-inflammatory activity) of 65-80 ng/mL. In some embodiments a dose of VX-745 provides a blood concentration of between about 15 and 45 ng/mL, or between 20 and about 40 ng/mL, or between about 25 and about 35 ng/mL, or between about 30 and about 40 ng/mL, wherein said blood concentration achieves inhibition of cytokine signaling.

In some embodiments, a composition is provided as a pharmaceutical formulation. In some embodiments, a pharmaceutical formulation is or comprises a unit dose amount for administration in accordance with a dosing regimen correlated with achievement of the reduced incidence or risk of disease.

In some embodiments, a formulation comprising provided compositions as described herein is administered as a single dose. In some embodiments, a formulation comprising provided compositions as described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising provided compositions as described herein is administered twice weekly, thrice weekly, every other day, daily, twice daily, or every eight hours.

The administration interval for a single individual need not be a fixed interval, but can be varied over time, depending on the needs of the individual.

In some embodiments, a formulation comprising provided compositions as described herein is administered at regular intervals. In some embodiments, a formulation comprising provided compositions as described herein is administered at regular intervals for a defined period. In some embodiments, a formulation comprising provided compositions as described herein is administered at regular intervals for 2 years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

Combination Therapies

In certain embodiments, the present invention provides a method of treating an ischemic injury comprising administering to a subject a dose of a p38-αMAPK inhibitor, such as VX-745, together with one or more additional therapeutic agents. In some embodiments, the present invention provides a method of treating a neurologic disorder comprising administering to a subject a therapeutically effective amount of VX-745 in combination with one or more additional therapeutic agents selected from cholinesterase inhibitors, N-methyl-D-aspartate antagonists, vitamin E, antidepressants, anxiolytics, antipsychotics, mood stabilizers and sleep aids.

Representative cholinesterase inhibitors include, without limitation, donepezil (Aricept®), rivastigmine (Exelon®), galantamine (Razadyne®) and tacrine (Cognex®). Representative antidepressants include, without limitation, bupropion (Wellbutrin®), citalopram (Celexa®), fluoxetine (Prozac®), mirtazapine (Remeron®), paroxetine (Paxil®), sertraline (Zoloft®), trazodone (Desyrel®), venlafaxine (Effexor®), nortriptyline (Pamelor®) and desipramine (Norpramine®). Representative anxiolytics include, without limitation, lorazepam (Ativan®) and oxazepam (Serax®). Representative antipsychotics include, without limitation, aripiprazole (Abilify®), clozapine (Clozaril®), haloperidol (Haldol®), olanzapine (Zyprexa®), quetiapine (Seroquel®), risperidone (Risperdal®) and ziprasidone (Geodon®). Representative mood stabilizers include, without limitation, carbamazepine (Tegretol®) and divalproex (Depakota®). Representative sleep aids include, without limitation, zolpidem, zaleplon and chloral hydrate. Representative N-methyl-D-aspartate antagonists include, without limitation, memantine (Namenda®).

In some embodiments, the present invention provides a method of treating an ischemic injury comprising administering to a subject a therapeutically effective amount of a p38-αMAPK inhibitor, such as VX-745, with one or more additional therapeutic agents selected from the group consisting of exenatide (Byetta®), varenicline, PF-04360365, rivastigmine, LY450139, ST101, bryostatin, EVP-6124, atomoxetine, HF0220, resveratrol, galantamine, PF-01913539, semagacestat, 3APS, immunoglobulin, dimebon, alpha-tocopherol, BAY85-8101, estrogen, progesterone, ACC-001, ginko biloba, nicergoline, piracetam, NIC5-15, xaliproden (SR57746A), indomethacin, DMXB-A, LY2062430, 11-C PIB, bapineuzumab, etanercept, ramipril, interferon beta-1a, simvastatin, lipoic acid, fish oil, curcumin, PF-04447943, folate, vitamin B6, vitamin B12, leuprolide, INM-176, AH110690, tryptophan, SK-PC-B70M, BMS-708163, escitalopram, TRx0014, BAY94-9172, cerebrolysin, epigallocatechin-galate, SB-742457, lithium, rosiglitazone, divalproex, SAR110894D, PRX-03140, CX516 (Ampalex), nicotinamide, rasagiline, AC-1202 (Ketasyn®), enduramide, neramexane, razadyne, NS 2330 (Tesofensine®), tamibarotene, acitretin, methylphenidate, mifepristone, ZT-1, AFFITOPE AD01, AFFITOPE AD02, GSK239512, GSK933776, SR57667B, PPI-1019, MPC-7869, AZD3480, PAZ-417, solanezumab, masitinib (AB1010), BAY1006578, docosahexaenoic acid, QS-21, MNI-558, reminyl retard, flutemetamol, estradiol, medroxyprogesterone, valproate, T-817MA, AZD1446, AAB-003 (PF-05236812), modafinil, raloxifene, atorvastatin, doxycycline, trazadone, sodium oxybate, huperzine A, lutein, zeaxanthin, AC-3933, dextroamphetamine, EPAX 1050TG, SRA-333, MNI-168, CAD106, SGS742, NP031112, SSR180711C, GSI-953, prazosin, MEM 1003, AndroGel, AVE1625, cyclophosphamate, TC-5619-238, MK0249, lecozotan, circadin, MEM 3454, PPI-1019, UB 311, PF-04494700, ABT-089, LY451395, E2020, Rofecoxib, PF-03654746, EHT 0202 etazolate, DCB-AD1, ONO-2506PO, EGb761®, gantenerumab, florbetapir, ELND005, prednisone, novasoy, ginseng, pioglitazone, caprylidene, ABT-288, ABT-384, nefiracetam, AQW051, Pitavastatin, naproxen sodium (Aleve®), lomoxicam, AN-1792, SR57667B, melatonin, SAM-531, MK0952, MK0677, IFN-alpha2A, BAY 94-9172, PYM50028, lecozotan SR, thalidomide, tramiprosate, FK962, IVIG, RO5313534, bifeprunox, LNK-754, ELND005, NSA-789, ramelteon, Florbetaben, SRA-444, VP4896, celecoxib, hydrocodone, GSI-136, Zolpidem, MK3328, metformin, CTS21166, elontril, ibuprofen, posiphen tartrate, JNJ-39393406, testosterone, BRL-049653, BMS-708163, SAM-315, ketoconazole, fluconazole, warfarin, E2609, AZD0328, LY2886721, CHF 5074, E2212, acetaminophen, LY2811376, ABT-126, melatonin, GSK1034702, armodafinil, depakote, gemfibrozil, AL-108, levetiracetam, and quinacrine.

EXEMPLIFICATION

Transient MCAO in Rats—Neurological and Functional Recovery

This example shows the efficacy of delayed treatment with VX-745 compound in enhancing functional sensorimotor recovery in the rat model of stroke. The endpoints of the study included mNSS score (Neuroscore), Stepping test (ST), Body swing test (BSW), Forelimb placing test (FLP), body weight measurements and brain harvesting.

Experimental Study Design
 Humane Endpoints
  No animal was found in a moribund condition or showed severe pain or enduring signs of severe distress.
 Study Initiation Definition
  tMCAO procedure day was defined as "DAY 1" of the study.
 Preparation and Anesthesia
  On the day of surgery anesthesia was induced with 4% isoflurane in a mixture of 70% $N_2O$ and 30% $O_2$ and maintained with 1.5-2% isoflurane.
 Animals
  Altogether 76 adult male Sprague Dawley rats, purchased from Harlan Laboratories, (Israel), and weighing 300-350 g were used for the experiment. Animals were housed at a standard temperature (20-24° C.) and in a light-controlled environment (12 hours light/12 hours dark) with ad libitum access to food and water.
Animals were grouped as follows:
 Group 1M: 20 tMCAO animals treated twice-a-day with vehicle from Day 3 (day 1 being day of stroke surgery) to Day 42 (via PO gavage)
 Group 2M: 22 tMCAO animals treated twice-a-day with VX-745 (1.5 mg/kg) from Day 3 (day 1 being day of stroke surgery) to Day 42 (via PO gavage)
 Group 3M: 21 tMCAO animals treated twice-a-day with VX-745 (4.5 mg/kg) from Day 3 (day 1 being day of stroke surgery) to Day 42 (via PO gavage)
Experimental Procedures
 Transient Middle Cerebral Artery Occlusion (tMCAO)
  Transient middle cerebral artery occlusion was performed according to the method described in R. Schmid-Elsaesser et al., *Stroke*, 29(10):2162-2170 (1998). The right Common Carotid Artery (CCA) was exposed through a midline neck incision and carefully dissected free from surrounding nerves and fascia—from its bifurcation to the base of the skull. The occipital artery branches of the ECA (External Carotid Artery) were then isolated, and these branches were dissected and coagulated. The ECA was dissected further distally and coagulated along with the terminal lingual and maxillary artery branches, which was then divided. The ICA (Internal Carotid Artery) was isolated and carefully separated from the adjacent vagus nerve, and the pterygopalatine artery was ligated close to its origin with a 5-0 nylon suture (SMI, Belgium). Next, a 4-0 silk suture was tied loosely around the mobilized ECA stump, and a 4 cm length of 4-0 monofilament nylon suture (the tip of the suture was blunted by using a flame, and the suture was coated with polylysine, prior to insertion) was inserted through the proximal ECA into the ICA and thence into the circle of Willis, effectively occluding the MCA. The surgical wound was closed and the animals were returned to their cages to recover from anesthesia. Two hours after occlusion rats were re-anesthetized, monofilament was withdrawn to allow reperfusion, surgical wound was closed and rats were returned to their cages.

24 hours post occlusion animals were subjected to neurological evaluation using the "Neuroscore for exclusion criteria". Only animals with an overall score of 10 were included in the study.

Test Items Administration 48 hours after reperfusion, all animals were treated by daily orally gavage two times per day.

Handling, Surgery, and Behavioral Testing Timetable

Animals were handled at a minimum for three days before the surgery. Baseline measures were taken before stroke was induced. Stroke surgery occurred on Day 1. On Day 2, 24 hours post-stroke surgery, Neuroscore testing was performed. Only animals reaching and exceeding Neuroscore criteria was included in the study. On Days 3-42, treatment with vehicle or VX-745 was administered twice a day for 40 days via PO (oral) gavage for all groups. Behavioral tests for all groups were conducted on weeks 4 and 6. Animals were sacrificed on Day 44 and brains were harvested.

Pre-Dosing Behavioral Habituation Testing

Limb Placing.

The limb placing tests were divided into forelimb and hindlimb tests. For the forelimb-placing test, the examiner holds the rat close to a tabletop and scores the rat's ability to place the forelimb on the tabletop in response to whisker, visual, tactile, or proprioceptive stimulation. Similarly, for the hindlimb placing test, the examiner assesses the rat's ability to place the hindlimb on the tabletop in response to tactile and proprioceptive stimulation. Separate sub-scores were obtained for each mode of sensory input and added to give total scores (for the forelimb placing test: 0=normal, 12=maximally impaired; for the hindlimb placing test: 0=normal; 6=maximally impaired). Scores were given in half-point increments (see below). Typically, there is a slow and steady recovery of limb placing behavior during the first month after stroke.

Forelimb placing test (0-12):
Whisker placing (0-2);
Visual placing (forward (0-2), sideways (0-2)
Tactile placing (dorsal (0-2), lateral (0-2)
Proprioceptive placing (0-2).
Stepping Test.

Animals were tested for forelimb akinesia in a stepping test (ST). The animal was held with its hind limbs fixed in one hand and the forelimb, not to be monitored, in the other, while the unrestrained fore-paw touches the table. The number of adjusting steps were counted while the animal was moved sideways along the table surface (85 cm during approximately five seconds), in the forehand & backhand direction for both forelimbs.

Body Swing Test.

The rat was held approximately one inch from the base of its tail. It was then elevated to an inch above a surface of the table. The rat was held in the vertical axis, defined as no more than 10° to either the left or the right side. A swing was recorded whenever the rat moved its head out of the vertical axis to either side. Before attempting another swing, the rat had must return to the vertical position for the next swing to be counted. Twenty (20) total swings were counted. A normal rat typically had an equal number of swings to either side. Following focal ischemia, the rat tends to swing to the contralateral side (left side in this case); as such, the test is a measure of "hemiparesis" (weakness on one side of the body). Body swing scores were expressed as a percentage of rightward over total swings.

Neurological Scoring (Neuroscore).

The individual performing the behavioral assessments was unaware of the drug/dose given (blinded testing). Neuroscore was performed according to a NSS table, which included motor tests, sensory tests, beam balance tests, and reflex absence and abnormal movement tests Samples Collection and Sacrifice The brains of all animals were harvested on Day 44. Rats were sacrificed by $CO_2$ inhalation. Brains were harvested from all animals in each group, divided to left and right hemisphere, weighed, and snap frozen.

IL-1β Analysis

Brains were harvested at study termination. Each brain was dissected into two hemispheres and each hemisphere was weighed and enclosed into tubes marked Left or Right. Each tube was immediately frozen in liquid nitrogen and stored at $(-80)°$ C. The tissues were defrosted and homogenized in 1 ml/200 mg tissue of 20 mM Tris-HCL pH 7.4 containing a protease inhibitor cocktail (50 μl/ml). Samples were centrifuged at 10,000 g for 15 min at 4°. Clear supernatants were aliquoted (150 μl/aliquot) and stored at $(-80)°$ C. until ELISA assays were performed. ELISA assay was executed according to kit instructions. Standards and samples were tested in duplicates.

Data Analysis

Statistical analysis was performed when applicable by two-way ANOVA for repeated measures, followed by Bonferroni post-hoc tests for all the data presented in the results section (*$p<0.05$; $p<0.01$; *$p<0.001$).

Results

A transient MCAO rat-stroke model was used in this study to evaluate the therapeutic activity of VX-745 compound. VX-745 was administered PO six times a week twice a day for 40 days, with the first administration performed 48 hours after reperfusion. Four different tests were employed in order to examine the efficacy of the tested compound, namely modified neurological severity score, body swing test, stepping test and forelimb placement test.

Mortality and Clinical Signs

Sixteen (16) rats died during the study. Thirteen rats died within 48 hours after stroke induction; while three rats died after treatment group allocation and treatment initiation. The three rats that died after treatment initiation all did so within two weeks of treatment initiation (two rats from group 1M and one rat from the group 2M).

Body Weight Monitoring

No statistically significant differences in body weight were observed in all groups through the study (FIG. 1). Two-way ANOVA statistics followed by Bonferroni post-hoc comparisons revealed no significant differences between the groups.

Neurological Test Score (Neuroscore)

Figure 2:
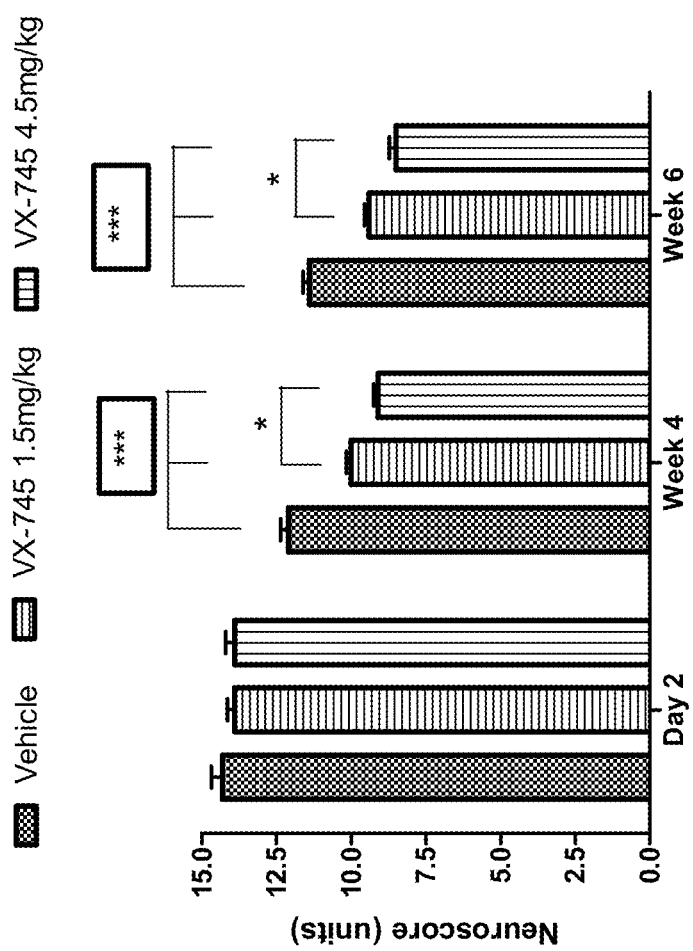
FIG. 2 depicts an exemplary graph showing neuroscores by group throughout a Transient Middle Cerebral Artery Occlusion study. A statistically significant difference in the neuroscore was found between Groups 2M and 3M (VX-745) compared to 1M (vehicle control), as well as between the two doses of groups 2M and 3M.
Figure 3:
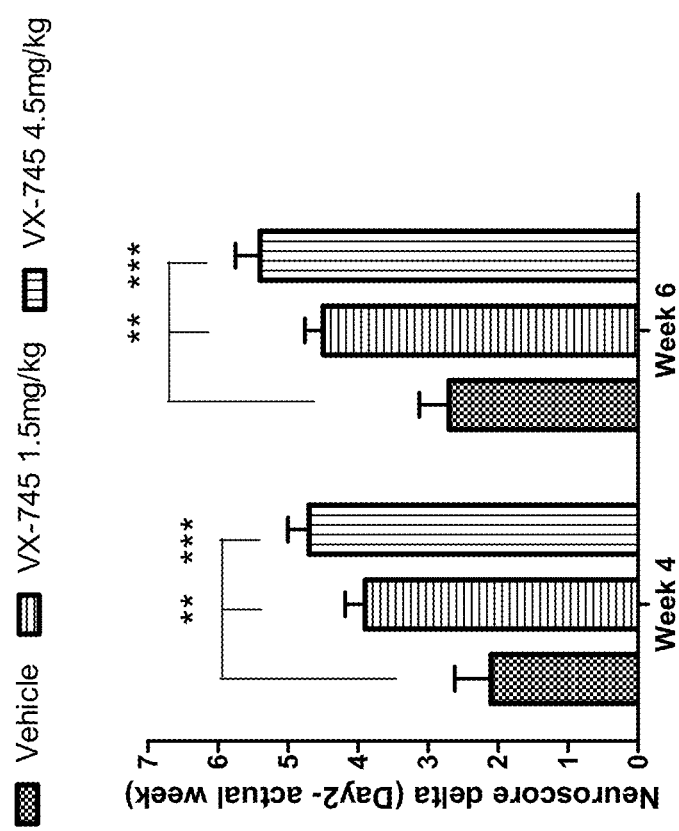
FIG. 3 depicts an exemplary graph showing the neuroscore delta (change from Day 2 to Week 4 or Week 6) by group throughout a Transient Middle Cerebral Artery Occlusion study. A statistically significant difference in neuroscore delta (Change from Day 2 to Week 4 or 6) was found between Groups 2M and 3M (VX-745) and 1M (vehicle control).

The Neuroscore included a set of clinical-neurological tests (composite of motor, sensory, reflex and balance tests) that were used to assess the effect of the tested treatments. Neuroscore was graded on a scale of 0 to 18 (in which normal score is 0 and maximal deficit score is represented by 18). As expected, a sharp decline in neurological functions was observed in all groups of rats 24 hours after tMCAO, with improvement observed over time thereafter. At Day 2, which was 24 hours after ischemia and 24 hours before initiation of treatment, there were no significant differences in neuroscore between treatment groups. However, statistically significant difference in absolute neuroscore at Weeks 4 and 6, and neuroscore delta (change from Day 2 to actual Week) was observed in Groups 2M and 3M treated with VX-745 PO when compared to the vehicle treated control group 1M. (FIG. 2 and FIG. 3)

Stepping Test Score

Figure 4:
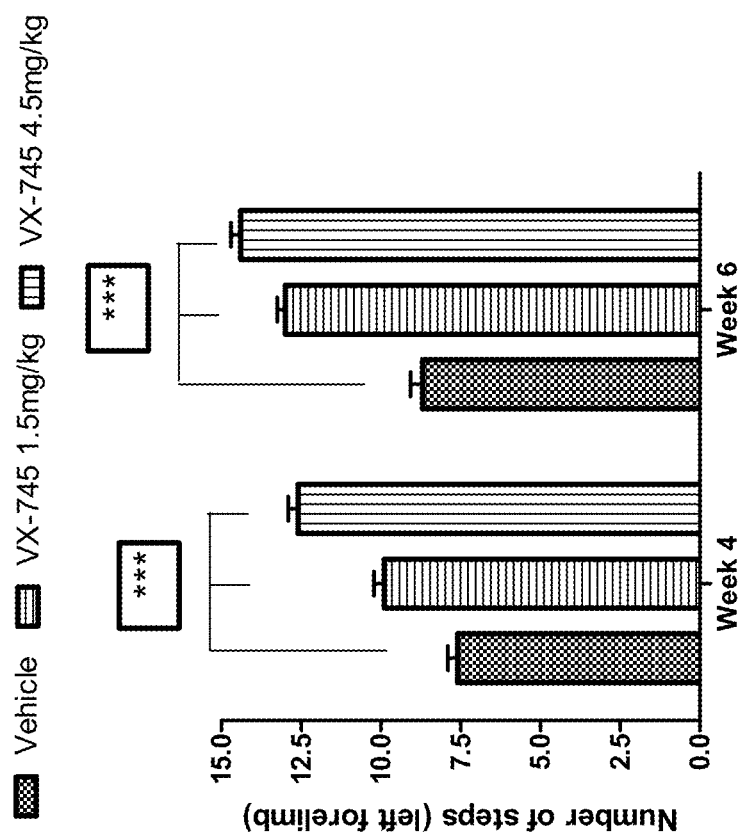
FIG. 4 depicts an exemplary graph showing the results of a stepping test (left forelimb) by treatment group throughout a Transient Middle Cerebral Artery Occlusion study. A statistically significant difference in number of steps was found between Groups 2M and 3M (VX-745) and 1M (vehicle control).

Animals were also tested for forelimb akinesia in the stepping test, commonly used for measurement of neuromuscular function, as an index for motor function of the animals. Improvement in motor function over time was observed in all animals that were subjected to tMCAO, mostly as a result of spontaneous functional recovery. However, functional improvement in rats treated with VX-745 in both tested doses was more pronounced compared to vehicle treated controls. Statistically significant differences in sensory motor deficit were observed between groups 2M and 3M treated with different doses of VX-745 versus vehicle treated control group 1M starting on Week 4 up to Week 6 (FIG. 4).

Forelimb Placement Test Score

Figure 5:
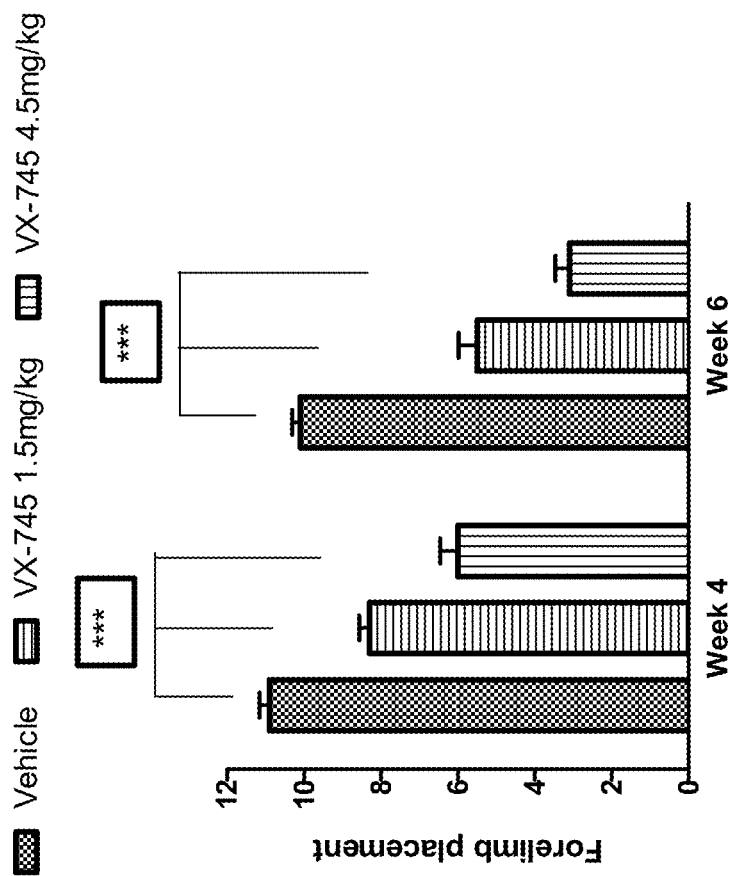
FIG. 5 depicts an exemplary graph showing the results of a forelimb placement test by treatment group throughout a Transient Middle Cerebral Artery Occlusion study. A statistically significant difference in the forelimb score was found between Groups 2M and 3M (VX-745) compared to group 1M (vehicle control).
Figure 6:
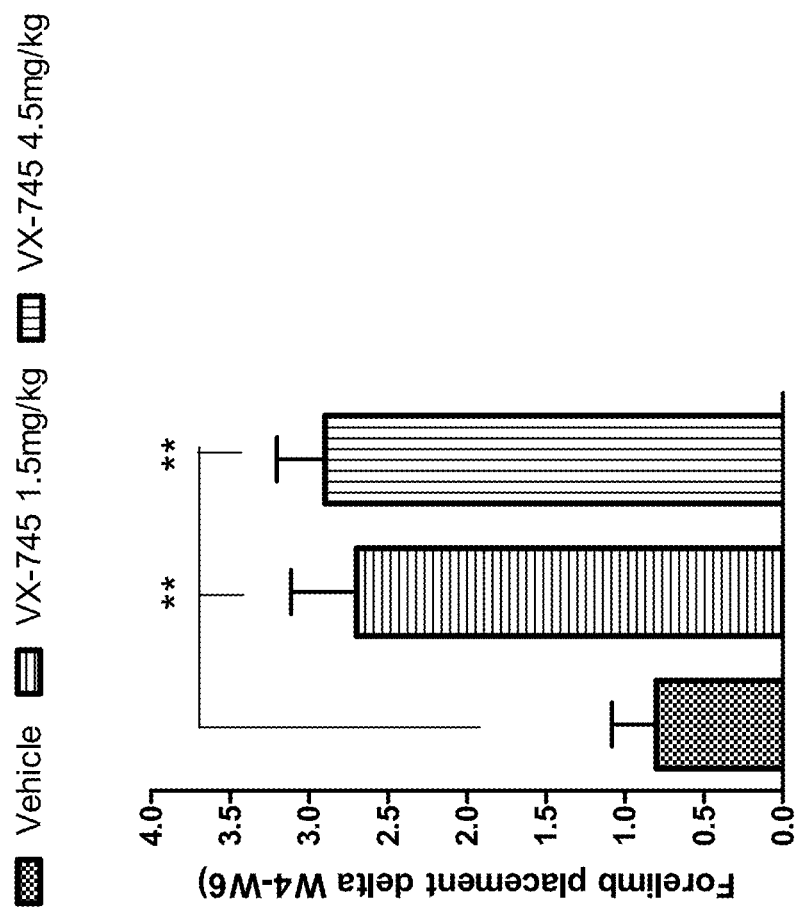
FIG. 6 depicts an exemplary graph showing the change in scores from Week 4 to Week 6 in a forelimb placement test throughout a Transient Middle Cerebral Artery Occlusion study. A statistically significant difference in score was found between Groups 2M and 3M (VX-745) compared to group 1M (vehicle control).

A forelimb placement test was used to measure somatosensory and sensory motor deficits. Similar to other tests, an improvement in sensory motor deficit over time was observed in all animals that were subjected to tMCAO, as a result of spontaneous functional recovery. However, functional improvement in all rats treated with different doses of VX-745 was observed, compared to vehicle treated control. Statistically significant differences in sensory motor improvement were observed between groups 2M and 3M treated with different doses of VX-745 versus vehicle treated control group 1M. This improvement was observed starting on Week 4 and Week 6 (FIG. 5 and FIG. 6).

Body Swing Test Score

Figure 7:
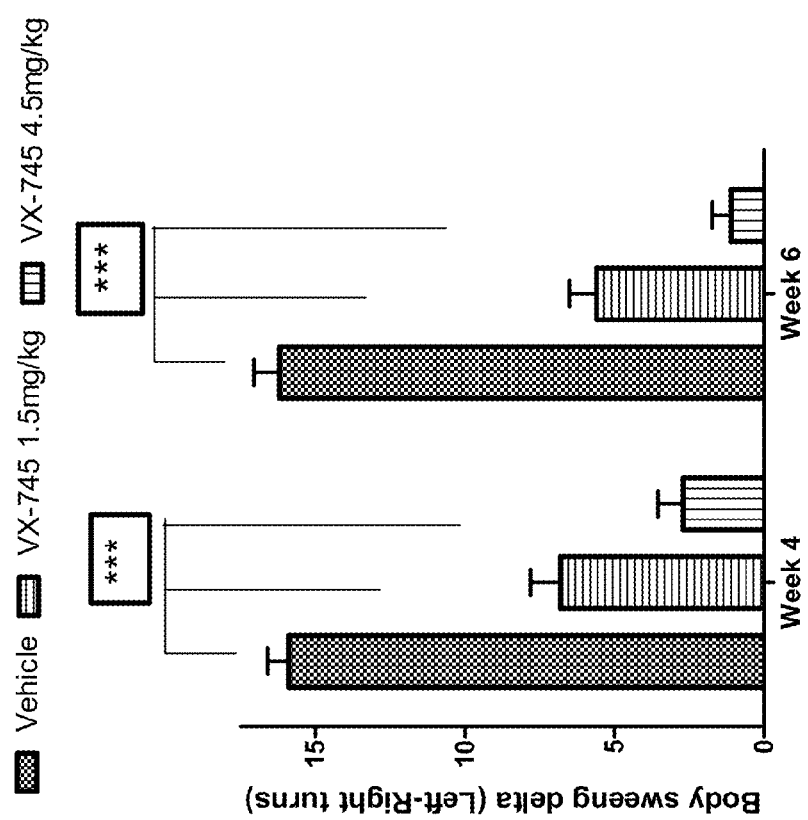
FIG. 7 depicts an exemplary graph showing the difference between left turn and right turn in a body swing test throughout a Transient Middle Cerebral Artery Occlusion study. A statistically significant difference in number of steps was found between Groups 2M and 3M (VX-745) and 1M (vehicle control).

Animals were also tested in the body swing test, commonly used for measurement of imbalance in neuromuscular functions. Improvement in motor function over time was observed in all animals that were subjected to tMCAO, mostly as a result of spontaneous functional recovery. In all rats treated with different doses of VX-745 more prominent functional improvement was observed, compared to vehicle treated control. Statistically significant differences were observed between groups 2M and 3M treated with different doses of VX-745 versus vehicle treated controls group 1M. (FIG. 7). Remarkably, there was near normalization in the body swing test, particularly in the 4.5 mg/kg dose group, suggesting a resolution of the one sided weakness that had otherwise developed in the animals with stroke induction.

IL-1β ELISA

Figure 8:
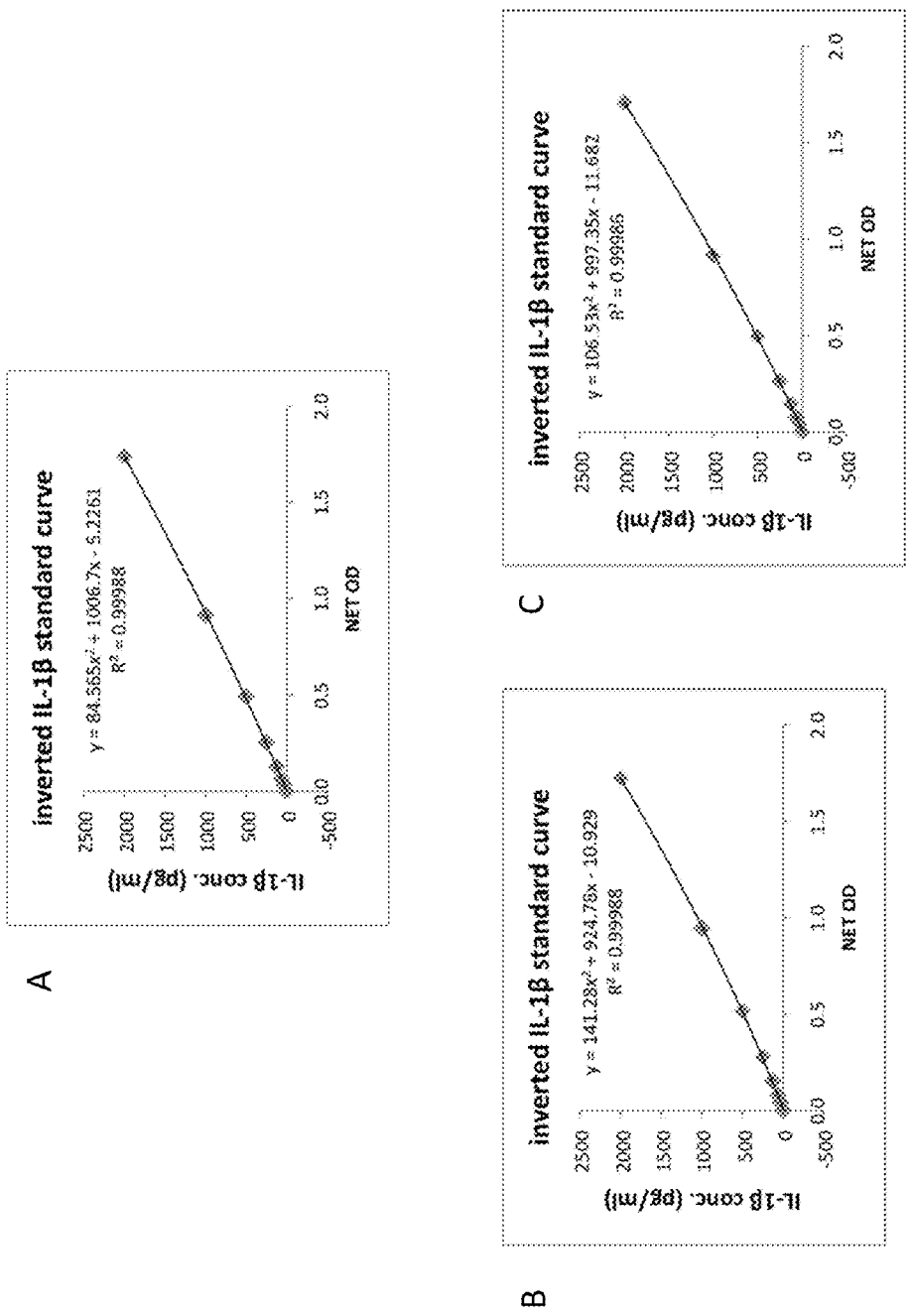
FIG. 8 depicts exemplary standard curves for three IL-1β ELISA assays (panels A, B and C).
Figure 9:
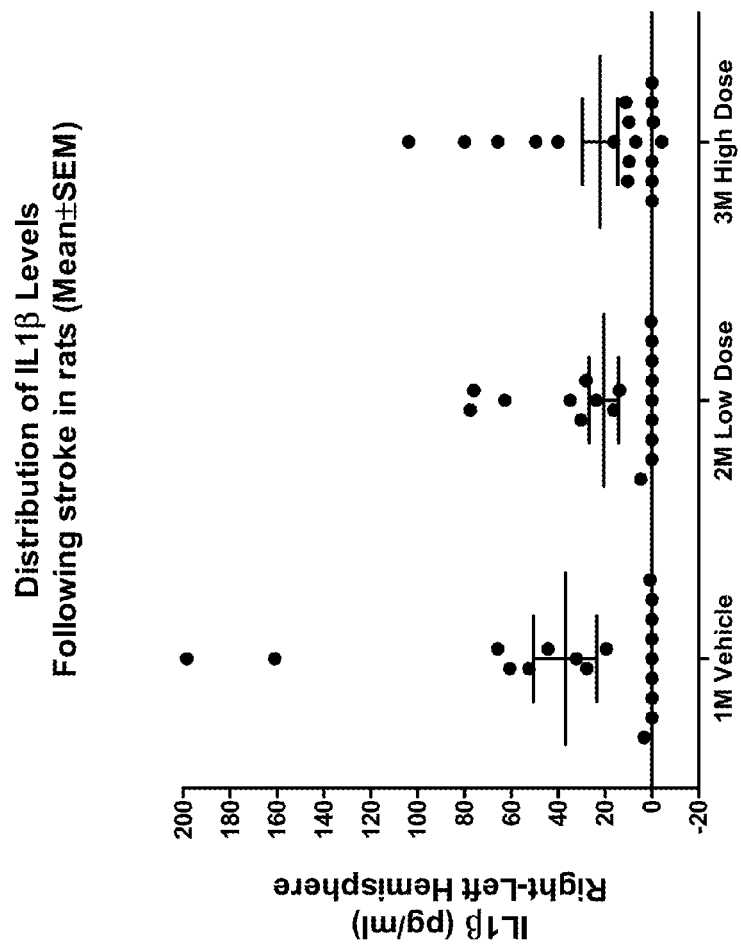
FIG. 9 depicts an exemplary graph showing IL-1β levels in the brain at the termination of a Transient Middle Cerebral Artery Occlusion study. No statistically significant differences were found between the groups. Despite the large variability of the results, these data do exhibit a trend, indicating the possibility of lower concentrations of IL-1β in the brains of the groups treated with VX-745.

Following study termination, animals were also tested for IL-1β brain levels using the ELISA system (see FIG. 8 for standard curves). The variability of the results was too large to allow definitive conclusions. All the results below the Lower Limit of Quantification (LLOQ) were assigned the LLOQ value of 5 pg/ml. Then, results for the uninjured left side were subtracted from the results of the right side. The distribution for individual rats is given in the figure below (n=18 in each of the study groups) (FIG. 9).

Discussion

The rat stroke tMCAO model is an accepted model for screening and evaluation of neuroprotective and rehabilitation efficacy of drug treatments. The model was used in this study to evaluate the efficacy of postponed VX-745 treatment. Rats were treated with VX-745 for 40 days at two doses via daily oral gavage, starting two days after the surgical procedure. During the study the neurological, motoric and somatosensory functions were monitored in a battery of behavioral tests.

As seen with human stroke, modest levels of spontaneous recovery of neurological functions was observed during the 42 days follow-up after stroke induction. However, clear differences were demonstrated between the groups treated with VX-745 compared to the vehicle treated control group. Greater improvement in motor functions compared to vehicle treated animals, evaluated by neuroscore, stepping test and body swing test, was demonstrated in animals that were treated with VX-745 with a trend to a dose-response relationship.

The observed function improvement is not attributable to differences in general rats' health, as all groups gained weight at the same rate with no significant differences between them (FIG. 1). In addition, no observed differences in general clinical signs were noted.

In view of these findings it may be concluded that under the conditions of the present study VX-745 treatment improved motor and somatosensory deficits in the rat stroke model to a greater extent than those treated with vehicle.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A method for promoting recovery of function in a subject that has suffered a neurologic injury, the method comprising administering to the subject a composition comprising VX-745 48 hours or greater after the onset of symptoms.

2. The method of claim 1, wherein the neurologic injury results from an acute ischemic stroke.

3. The method of claim 2, wherein the stroke is a thrombotic stroke or an embolic stroke.

4. The method of claim 2, wherein the step of administering is initiated at or greater than 72 hours after onset of stroke symptoms.

5. The method of claim 2, wherein the step of administering comprises administration of a composition comprising VX-745 at a regular interval.

6. The method of claim 5, wherein the regular interval is selected from the group consisting of, twice weekly, thrice weekly, daily, twice daily, and every eight hours.

7. The method of claim 1, wherein the step of administering comprises oral administration.

8. A method for promoting neurologic recovery from ischemic injury in a subject, the method comprising administering to the subject a composition comprising VX-745.

9. The method of claim 8, wherein the ischemic injury is caused by a stroke.

10. The method of claim 9, wherein the step of administering is initiated at or greater than 24 hours after onset of stroke symptoms.

11. The method of claim 9, wherein the step of administering is initiated at or greater than 48 hours after onset of stroke symptoms.

12. The method of claim 9, wherein the step of administering is initiated at or greater than 72 hours after onset of stroke symptoms.

13. The method of claim 8, wherein the step of administering comprises administration of a composition comprising VX-745 at a regular interval.

14. The method of claim 8, wherein the step of administering comprises oral administration.

15. The method of claim 1, wherein the composition comprising VX-745 is administered at a dose providing a blood concentration of between about 15 ng/mL to about 45 ng/mL.

16. The method of claim 15, wherein the dose is between about 1 mg to about 125 mg of VX-745 per day.

17. The method of claim 8, wherein the composition comprising VX-745 is administered at a dose providing a blood concentration of between about 15 ng/mL to about 45 ng/mL.

18. The method of claim 17, wherein the dose is between about 1 mg to about 125 mg of VX-745 per day.

* * * * *